United States Patent [19]

Gauthier et al.

[11] Patent Number: 4,492,697

[45] Date of Patent: Jan. 8, 1985

[54] 4H-IMIDAZO[2,3-C]PYRIDO[2,3-E][1,4]OXAZINE DERIVATIVES

[75] Inventors: Jean A. Gauthier; Ivo L. Jirkovsky, both of Montreal, Canada

[73] Assignee: Ayerst, McKenna & Harrison, Inc., Montreal, Canada

[21] Appl. No.: 523,989

[22] Filed: Aug. 16, 1983

[51] Int. Cl.³ .................. A61K 31/535; C07D 498/14
[52] U.S. Cl. ........................... 424/248.4; 424/248.54; 424/248.55; 544/101; 544/105
[58] Field of Search .................. 544/101; 424/248.54, 424/248.55, 248.4

[56] References Cited

U.S. PATENT DOCUMENTS 4,145,419 3/1979 Rowlands et al. ............... 424/248.4

Primary Examiner—Richard L. Raymond

[57] ABSTRACT

The invention discloses novel 4H-imidazo[2,3-c]pyrido[2,3-e][1,4]oxazine derivatives, processes for their preparation, pharmaceutical compositions thereof and methods for using the compounds. The compounds of this invention are useful in the treatment of anaphylactic reactions and allergic conditions in a mammal.

7 Claims, No Drawings

4H-IMIDAZO[2,3-C]PYRIDO[2,3-E][1,4]OXAZINE DERIVATIVES

BACKGROUND OF THE INVENTION

This invention relates to novel 4H-imidazo[2,3-c]pyrido[2,3-e][1,4]oxazine derivatives to processes for their preparation, to methods of using the derivatives and to pharmaceutical compositions of the derivatives. The compounds of this invention are useful in the treatment of anaphylactic reactions and allergic conditions in mammals.

The compounds of this invention have a novel 4H-imidazo[2,3-c]pyrido[2,3-e][1,4]oxazine ring system. The closest related and known ring system is illustrated by the imidazobenzoxazine derivatives described by D. A. Rowlands et al., U.S. Pat. No. 4,145,419, Mar. 20, 1979. The compounds of this invention are distinguished from the known compounds by having a different ring system and different substituents on the ring system.

SUMMARY OF THE INVENTION

The compounds of this invention are represented by formula I

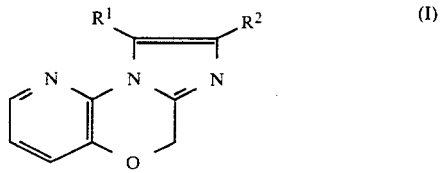

in which $R^1$ and $R^2$ are hydrogen, or $R^1$ is amino and $R^2$ is $COR^3$ wherein $R^3$ is lower alkoxy, lower alkylamino, di(lower alkyl)amino, 1-pyrrolidinyl or 1-piperidinyl, or a therapeutically acceptable acid addition salt thereof.

A preferred group of compounds is represented by formula I in which $R^1$ and $R^2$ are hydrogen, or $R^1$ is amino and $R^2$ is lower alkoxycarbonyl or 1-pyrrolidinylcarbonyl, or a therapeutically acceptable acid addition salt thereof.

The compounds of this invention are useful for preventing or treating anaphylactic reactions or allergic conditions in a mammal by administering to the mammal an effective anaphylaxis alleviating or allergy alleviating amount of a compound of formula I.

The compounds of this invention form a pharmaceutical composition which comprises a compound of formula I and a pharmaceutically acceptable carrier.

DETAILED DESCRIPTION OF THE INVENTION

The term "lower alkyl" as used herein means straight and branched chain alkyl radicals containing from one to six carbon atoms, preferably one to three carbon atoms, and includes methyl, ethyl, propyl, 1-methylethyl, butyl, 1,1-dimethylethyl, pentyl and the like, unless stated otherwise.

The term "lower alkoxy" as used herein means straight chain alkoxy radicals containing from one to six carbon atoms and branched chain alkoxy radicals containing three to six carbon atoms and includes methoxy, ethoxy, 1-methylethoxy, butoxy, hexoxy and the like.

The term "lower alkanol" as used herein means both straight and branched chain alkanols containing from one to four carbon atoms and includes methanol, ethanol, 1-methylethanol, butanol and the like.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic, acetic, maleic, methanesulfonic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The compounds of this invention of formula I are useful in the prevention or treatment of allergic reactions in a mammal.

More specifically, the compounds of this invention are useful for the prophylactic treatment as well as for the management of anaphylactic reactions and atopic allergic manifestations, for example, bronchial asthma, hay fever, allergic rhinitis, allergic conjunctivities, food allergies, urticaria and the like, in a sensitized mammal.

The prevention or treatment of allergic reactions in a mammal by administration of a compound of formula I is demonstrated by using known anti-allergic tests in an appropriate animal model.

In one such test for the determination of useful anti-allergic activity, the compounds of formula I are tested using the passive paw anaphylaxis (PPA) method, described by R. R. Martel and J. Klicius, Int. Archs. Allergy Appl. Immun., 54, 205 (1977). In this method, reaginic antibody-induced hypersensitivity is produced in the rat hindpaw. Increased vascular permeability is determined by measuring the increase in paw volume. An effective anti-allergic drug inhibits the increase in paw volume when compared to the untreated reaginic hypersensitive controls. In this test, the following illustrative compounds of formula I are effective anti-allergic agents when administered at an intraperitoneal dose of 30 mg/kg of body weight: 4H-imidazo[2,3-c]pyrido[2,3-e][1,4]oxazine hydrochloride causes a 23% inhibition at 15 minutes of the increase in paw volume; 2-[1-(pyrrolidinyl)carbonyl]-4H-imidazo[2,3-c]pyrido[2,3-e][1,4]oxazine-1-amine causes a 20% inhibition at 15 minutes of the increase in paw volume; and 1-amino-4H-imidazo[2,3-c]pyrido[2,3-e][1,4]oxazine-2-carboxylic acid, ethyl ester causes a 30% inhibition at 15 minutes of the increase in paw volume.

When the compounds of formula I of this invention are used for suppressing allergic manifestations of anaphylactic reactions and atopic hypersensitivity in a mammal, they are used alone or in combination with pharmacologically acceptable carriers, the proportion of which is determined by the solubility and the chemical nature of the compound, chosen route of administration and standard biological practice.

For example, they are administered orally in solid form i.e. capsule or tablet. They can also be administered orally in the form of suspensions or solutions or they may be injected parenterally. They can be administered parenterally by the nasal route, for instance, as drops or aerosol; or by inhalation from an aerosol.

In addition, the compounds of this invention can be administered in conjunction with common anti-allergic agents, for example, known compounds effecting antihistaminic, analgesic, central nervous system depressant, anti-hypertensive, immunosupressive, anti-bradykinin, anti-serotonin or endocrinological responses.

The tablet compositions for oral administration contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I for oral administration contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions for oral administration can be formulated by suspending the active ingredient in ethyl alcohol, in a vegetable oil, for example, arachis oil, olive oil, sesame oil, or coconut oil, or in a mineral oil, for example liquid paraffin, and the suspension may contain a thickening agent, for example beeswax or hard paraffin. These compositions can also contain a sweetening agent, flavoring agent and antioxidant.

For administration to a mammal by parenteral injection, it is preferred to use the compounds of formula I in solution in a sterile aqueous vehicle which may also contain other solutes, such as buffers or preservatives, as well as sufficient quantities of pharmaceutically acceptable salts or of glucose to make the solution isotonic.

The compounds of formula I can also be administered as nasal powders or insufflations. For such purpose, the compounds are administered in finely divided solid form together with a pharmaceutically acceptable solid carrier, for example, a finely divided polyethylene glycol (e.g. "Carbowax 1540") or finely divided lactose. Such compositions may also contain other excipients in finely divided solid form.

For administering the compounds of this invention by inhalation from an aerosol, the compound of formula I is dissolved in water or ethanol and mixed with a volatile propellant, for example, dichlorotetrafluoroethane and dichlorodifluoromethane, and placed in a pressurized container having a metering valve to release a predetermined amount of material.

The dosage of the compounds of formula I as anti-allergic agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compounds of this invention are most desirably administered at a concentration level that will generally afford effective results without causing any harmful or deleterious side effects. For example, an effective anti-allergic amount of a compound of formula I usually ranges from about 0.1 mg to about 500 mg per kg of body weight per day in single or divided doses, although as aforementioned, variations will occur. However, a dosage level that is in the range from about 0.5 mg to about 200 mg per kg of body weight per day in single or divided dose is employed most desirably in order to achieve effective results.

The following reaction scheme illustrates a method for preparing the compounds of formula I:

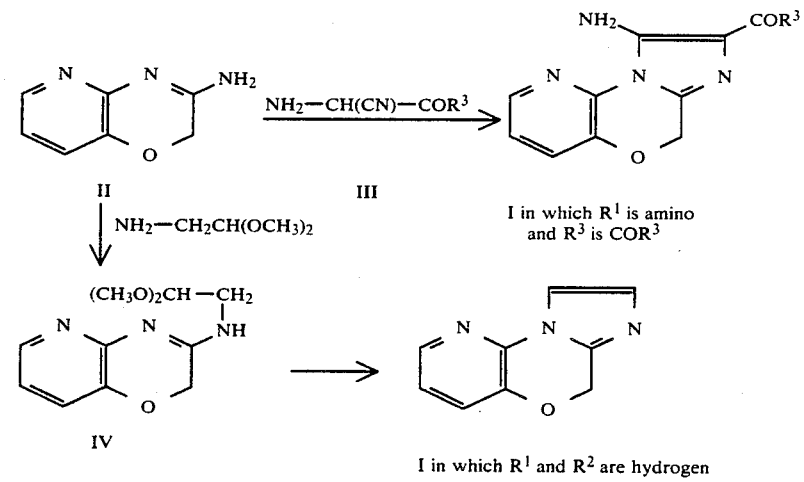

With reference to the above reaction scheme, the compounds of formula I are prepared by:

(a) condensing the compound of formula II with a compound of formula III in which $R^3$ is as defined herein to obtain the corresponding compound of formula I in which $R^1$ is amino and $R^2$ is $COR^3$ wherein $R^3$ is as defined herein; or (b) condensing the compound of formula II with $NH_2-CH_2CH(OCH_3)_2$ to obtain the corresponding compound of formula IV and cyclizing the compound of formula IV to obtain the compound of formula I in which $R^1$ and $R^2$ are hydrogen.

More specifically, the compound of formula I in which $R^1$ is amino and $R^2$ is $COR^3$ is prepared by condensing the compound of formula II with about one to two molar equivalents of the compound of formula III at about 50° to 100° C. for about four to ten hours in a lower alkanol, preferably methanol, ethanol or propanol.

The compound of formula I in which $R^1$ and $R^2$ are hydrogen is prepared by condensing the compound of formula II with about 1.5 to 2.0 molar equivalents of $NH_2-CH_2CH(OCH_3)_2$ at about 70° to 80° C. for about three to six hours in a lower alkanol, preferably ethanol, to obtain the compound of formula IV. Cyclization of the compound of formula IV with about 2.0 to 2.5 molar equivalents of titanium tetrachloride at about 90° to 130° C. for about two to four hours in an inert organic solvent, preferably toluene, gives the compound of formula I in which $R^1$ and $R^2$ are hydrogen.

The following examples illustrate further this invention.

EXAMPLE 1

4H-Imidazo[2,3-c]pyrido[2,3-e][1,4]oxazine (I: $R^1$ and $R^2=H$)

2-Amino-3-pyridinol (11.0 g, 100 mmoles) was dissolved in acetonitrile (100 mL) and refluxed in the presence of anhydrous potassium carbonate (10.0 g) and chloroacetonitrile, (9.0 g, 120 mmoles). After stirring for 6 hours under these conditions, the white suspension was filtered off and the clear solution was concentrated, the crude residue was dissolved in chloroform and filtered through a silica gel column. Elution with the same solvent yielded an orange solid (8.35 g). Crystallization of the material using ethyl acetate-hexane yielded (2-amino-3-pyridinyloxy)acetonitrile (7.15 g): mp 100°–101° C.; Anal. Calcd for $C_7H_7N_3O$: C, 56.37% H, 4.73% N, 28.18% and Found: C, 56.69% H, 4.58% N, 28.17%; UV max (MeOH) 297 nm ($\epsilon$ 6,060) and 234 (10,080); and NMR $(CDCl_3)\delta$ 4.78 (m, 4H) and 6.5–7.8 (m, 3H).

The latter compound (5.0 g, 33.6 mmoles) was refluxed in ethanol (50 mL) containing 2.2 meq of freshly prepared sodium ethoxide. The solvent was evaporated, and the residue was triturated with ethyl acetate to afford a yellow powder (3.5 g) mp 170°–171° C. Recrystallization from isopropanol afforded 3-amino-2H-pyrido[3,2-b][1,4]oxazine: mp 173°–174° C.; Anal. Calcd for $C_7H_7N_3O$: C, 56.37% H, 4.73% N, 28.18% and Found: C, 56.40% H, 4.80% N, 28.33%; UV max (MeOH) 308 nm ($\epsilon$ 14,430) and 265 (4,740); and NMR (DMSO-$d_6$) $\delta$ 4.5 (s, 2H), 6.9 (m, 2H), 7.3 (s, 2H), 7.8 (m, 1H).

The latter compound (10.0 g, 67.0 mmoles) and aminoacetaldehyde dimethylacetal (7.05 g, 123 mmoles) were refluxed in ethanol (100 mL) for 5 hours. The solvent was evaporated and the residue which dissolved in 1:10 methanol-chloroform was chromatographed on silica gel column with the same solvent combination to yield a brown solid mp 136°–137° C. (13.08 g) which was recrystallized from ethyl acetate to give N-(2H-pyrido[3,2-][1,4]oxazin-3-yl)aminoacetaldehyde dimethylacetal: mp 136°–37° C.; Anal. Calcd for $C_{11}H_{15}N_3O_3$: C, 55.68% H, 6.37% N, 17.71% and Found: C, 55.57% H, 6.44% N, 17.68%; UV max (MeOH) 312 nm ($\epsilon$ 16,860), and 267 (6,520); and NMR $(CDCl_3)$ $\delta$ 3.4 (s, 6H), 3.7 (m, 2H), 4.53 (m, 3H), 5.6 (br, 1H), 6.9 (m, 2H), 7.95 (m, 1H).

The latter compound (6.7 g, 28.2 mmoles) was heated in boiling toluene (500 mL) until it dissolved and then titanium tetrachloride (6.5 mL, 11.22 g, 59.2 mmoles) was added to the mechanically stirred solution under nitrogen. The resulting suspension was continued to stir under these conditions for 3 hours. The cooled mixture was treated with water (200 mL); the two phase-system was filtered to remove insoluble material. The colorless toluene phase was separated from the aqueous phase, the latter of which was basified using aqueous potassium carbonate. The aqueous phase was extracted with methylene chloride and the organic extract was washed with brine, dried (MgSO$_4$) and evaporated to yield a pale yellow powder of the title compound (4.10 g). A solution of hydrogen chloride in diethyl ether was added in excess to a diethyl ether solution of the bulk of the free base. The white precipitate was collected by filtration and recrystallized from acetic acid-hexane to afford the hydrochloride salt of the title compound (4.13 g): mp 295°–297° C.; Anal. Calcd for $C_9H_7N_3O.HCl$: C, 51.56% H, 3.85% N, 20.04% and Found: C, 51.63% H, 3.67% N, 20.08%; UV max (MeOH) 293 nm ($\epsilon$ 9,668); NMR $(CDCl_3)$ of the title compound free base: $\epsilon$ 5.35 (s, 2H), 7.5 (m, 5H).

EXAMPLE 2

2-[1-(Pyrrolidinyl)carbonyl]-4H-imidazo[2,3-c]pyrido[2,3-e][1,4]oxazine-1-amine (I: $R^1$=amino and $R^2$=1-pyrrolidinylcarbonyl)

3-Amino-2H-pyrido[3,2-b][1,4]oxazine (described in Example 1, 8.50 g, 57 mmoles) and amino[(1-pyrrolidinyl)carbonyl]acetonitrile (11.35 g, 74 mmoles) was refluxed in ethanol (65 mL) for 6 hr. The mixture was cooled in ice-water and the precipitate was collected by filtration and recrystallized from glacial acetic acid-hexane to give a beige powder (3.75 g) of the title compound: mp 207°–208° C.; Anal. Calcd for $C_{14}H_{15}N_5O_3$: C, 58.93% H, 5.30% N, 24.55% and Found: C, 58.95% H, 5.32% N, 24.72%; IR (mineral oil) 3420, 3320 and 1590 cm$^{-1}$; UV max (MeOH) 281 nm ($\epsilon$ 19,515), 237 (13,750); NMR (DMSO-$d_6$) $\delta$ 1.8 (m, 4H), 3.65 (m, 4H), 5.2 (s, 2H), 6.85 (s, 2H) 7.4 (m, 2H), 8.05 (m, 1H).

EXAMPLE 3

1-Amino-4H-imidazo[2,3-c]pyrido[2,3-e][1,4]oxazine-2-carboxylic Acid, Ethyl Ester (I: $R^1$=amino and $R^2$=ethoxycarbonyl)

3-Amino-2H-pyrido[3,2-b][1,4]oxazine (described in Example 1, 8.0 g, 53.6 mmoles) and 2-amino-2-cyanoacetic acid, ethyl ester (8.0 g, 62.4 mmoles) were stirred in refluxing ethanol (100 mL) for 9 hr. A tan powder (4.6 g) was obtained upon cooling of this mixture. Filtration and recrystallization from isopropanol afforded the title compound (1.31 g): mp 155° C.; Anal. Calcd for $C_{12}H_{12}N_4O_3$: C, 55.38% H, 4.65% N, 21.53% and Found: C, 55.30% H, 4.73% N, 21.85%; IR (CHCl$_3$) 3460, 3340, 1670$^{-1}$; UV max (MeOH) 289 nm ($\epsilon$ 15,805), 270 (16,065), 237 (8,785); NMR $(CDCl_3)$ $\delta$ 1.4

(t, 3H), 4.35 (q, 2H), 5.15 (s, 2H), 6.65 (s, 2H), 7.25 (m, 2H), 8.0 (m, 1H).

We claim:

1. A compound of the formula

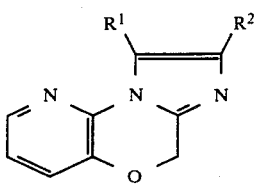

in which $R^1$ and $R^2$ are hydrogen, or $R^1$ is amino and $R^2$ is $COR^3$ wherein $R^3$ is lower alkoxy, lower alkylamino, di(lower alkyl)amino, 1-pyrrolidinyl or 1-piperidinyl, or a therapeutically acceptable acid addition salt thereof.

2. A compound of claim 1 wherein $R^1$ and $R^2$ are hydrogen, or $R^1$ is amino and $R^2$ is lower alkoxycarbonyl or 1-pyrrolidinylcarbonyl, or a therapeutically acceptable acid addition salt thereof.

3. The compound of claim 2, which is 4H-imidazo[2,3-c]pyrido[2,3-e][1,4]oxazine.

4. The compound of claim 2, which is 2-[1-(pyrrolidinyl)carbonyl]-4H-imidazo[2,3-c]pyrido[2,3-e][1,4]oxazine-1-amine.

5. The compound of claim 2, which is 1-amino-4H-imidazo[2,3-c]pyrido[2,3-e][1,4]oxazine-2-carboxylic acid, ethyl ester.

6. A method of preventing or treating anaphylactic reactions or allergic conditions in a mammal, which comprises administering to said mammal an effective anaphylaxis alleviating or allergy alleviating amount of a compound of claim 1.

7. A pharmaceutical composition, which comprises a compound of claim 1 and a pharmaceutically acceptable carrier.

* * * * *